(12) United States Patent
Hsu et al.

(10) Patent No.: US 6,251,663 B1
(45) Date of Patent: Jun. 26, 2001

(54) RECOMBINANT EUKARYOTIC PLASMIDS CONTAINING ALLERGEN-GENE AND USE THEREOF FOR THE PREVENTION AND/OR TREATMENT OF ALLERGIC DISEASES

(75) Inventors: Ching-Hsiang Hsu, Kao-Hsiung; Kaw-Yan Chua, Taipei; Mi-Hua Tao, Hsien; Kue-Hsiung Hsieh, Taipei, all of (TW)

(73) Assignee: Jen Wen Co., Ltd. (TW)

( * ) Notice: Subject to any disclaimer, the term of this patent is extended or adjusted under 35 U.S.C. 154(b) by 0 days.

(21) Appl. No.: 09/166,967

(22) Filed: Oct. 6, 1998

Related U.S. Application Data

(63) Continuation of application No. 08/682,837, filed on Jul. 12, 1996, now Pat. No. 5,958,891.

(30) Foreign Application Priority Data

Apr. 24, 1996 (TW) .................................. 85104888

(51) Int. Cl.$^7$ ............................ A61K 31/70; C12N 15/74
(52) U.S. Cl. .................. 435/320.1; 435/458; 435/455; 435/375; 514/44
(58) Field of Search .............................. 435/320.1, 375, 435/325

(56) References Cited

U.S. PATENT DOCUMENTS

| 5,550,017 | * | 8/1996 | Compans | .................................. 435/5 |
| 5,580,859 | | 12/1996 | Felgner et al. | .......................... 514/44 |
| 5,589,466 | | 12/1996 | Felgner et al. | .......................... 514/44 |
| 5,830,686 | * | 11/1998 | Henderson | ........................... 435/69.1 |

FOREIGN PATENT DOCUMENTS

| 95/05853 | 3/1995 | (WO) . |
| 95/20606 | 8/1995 | (WO) . |
| 96/13277 | 5/1996 | (WO) . |

OTHER PUBLICATIONS

Yang et al. Biochemical and Biophysical Research Communications, 212(3):1029–1039.
Hsu et al., Nature Medicine, 2(5):540–544.
Dittrich et al., Bio/Technology, 12(6):614–618.
Fred D. Ledley, "Non–viral gene therapy" Current Opinion in Biotechnology 1994 5:626–636.
J.P. Schofield and C.T. Caskey "Non–viral approaches to gene therapy" British Medical Bulletin (1995) vol. 5, No. 1 pp. 56–71.
Campbell et al., J. Immunological Methods, 188:73–78.
Raz et al., Proc. Natl. Acad.Sci. USA, 93:5141–5145.
Hsu et al., International Immunology, 8(9):1405–1411.
Raz et al., J. Allergy and Clinical Immunology, 97(1 Part 3):362.
Sporik et al., 1990, "Exposure to house dust mite allergen (Der p 1) and the development of asthma in childhood: a prospective study" New England J. Med. 323:502–507.

Platt–Mills et al., 1992, "Dust mite allergens and asthma: report of the 2nd international workshop" J. Allergy Clin. Immunol. 89:1046–1060.
Burrows et al., 1989, Association of asthma with serum IgE levels and skin–test reactivity to allergens: New England J. Med. 320:271–277.
Sears et al., 1991, "Relation between airway responsiveness and serum IgE in children with asthma and in apparently normal children" New England J. Med. 325:1067–1071.
Hsieh, K.H., 1984, Changes of lymphoproliferative response of T cell subsets to allergen and mitogen after hyposensitization in asthmatic children: J. Allergy Clin. Immunol. 74:34–40.
Gonzalez et al., 1987, "Allergen–induced recruitment of bronchoaveolar helper (OKT4) and suppressor (OKT8) T–cells in asthma" Am. Rev. Respir. Dis. 136:600–604.
Sedgwick et al., 1985, "Induction of IgE secreting cells and IgE isotype–specific suppressor cells in the respiratory lymph nodes of rats in response to antigen inhalation" Cell. Immunol. 94:182–194.
Kemeny et al., 1991, "Role of CD8 T–cells in rat IgE responses" Int. Arch. Allergy Appl. Immunol. 94:99–101.
McMenamin et al., 1993, "The natural immune response to inhaled soluble protein antigens involves major histocompatability complex (MHC) class–restrictted CD8+ T cell–mediated but not MHC Class II–restricted CD4+ T cell–dependent immune deviation resulting in selective suppression of immunoglobulin production" J. Exp. Med. 178:889–899.
Renz et al., 1994, "Inhibition of IgE production and normalization of airway responsiveness by sensitized CD8 T cells in a mouse model of allergen–induced sensitization" J. Immunol. 152:351–360.
Wolff et al., 1990, "Direct gene transfer into mouse muscle in vivo" Science 247:1465–1468.
Tang et al., 1992, "Genetic immunization is a simple method for illiciting an immune response" Nature 356:152–154.

(List continued on next page.)

Primary Examiner—Karen M. Hauda
Assistant Examiner—Joseph T. Woitach
(74) Attorney, Agent, or Firm—Banner & Witcoff, Ltd.

(57) ABSTRACT

The present invention relates to recombinant eukaryotic plasmids comprising an eukaryotic expression vector and an allergen gene for the prevention and/or treatment of allergic diseases. When the recombinant vector containing allergen-gene administrate to an individual in need of such prevention and/or treatment by intramuscular injection, intranasal delivery or intratracheal delivery, the production of allergen-specific IgE synthesis can be inhibited. The invention also relates to the pharmaceutical compositions comprising the the recombinant vector for use in the the prevention and/or treatment of allergic diseases and the production of allergen-specific IgE synthesis. A method for the prevention and/or treatment of allergic diseases is also provided.

4 Claims, 10 Drawing Sheets

(2 of 10 Drawing Sheet(s) Filed in Color)

OTHER PUBLICATIONS

Holt et al., 1987, "Suppression of IgE responses following antigen inhalation: a natural homeostatic mechanism which limits sensitization to aeroallergens" Immunol. Today 8:14–18.

Kemeny et al., 1994, "Immune regulation: a new role for the CD8+ T cell" Immunol. Today 15:107–110.

Keh–Liang Lin et al., 1994, "Allergens, IgE, Mediators, inflammatory mechanisms: Characterization of Der p V allergen, cDNA analysis, and IgE–mediated reactivity to the recombinant protein" J. Allergy Clin. Immunol. 94:989–996.

Chua et al. "Production of recobinant mite allergens," Mol. Biol. Immunol. Allergens (Ed. Kraft et al.) CRC, Boca Raton, Fla., pp. 135–138, 1993.*

* cited by examiner

RECOMBINANT EUKARYOTIC PLASMIDS CONTAINING ALLERGEN-GENE AND USE THEREOF FOR THE PREVENTION AND/OR TREATMENT OF ALLERGIC DISEASES

This application is a continuation of U.S. Ser. No. 08/682,837, filed Jul. 12, 1996, now U.S. Pat. No. 5,958,891, issued Sep. 28, 1999, which claimed the benefit under 35 U.S.C. § 119 of Republic of China (Taiwan) Patent Application No. 85104888, filed Apr. 24, 1996.

BACKGROUND OF THE INVENTION

Allergic diseases (AD) including allergic rhinitis, asthma and atopic dermatitis affect about 20% of the population and are important causes of morbidity and mortality. Most allergic diseases are found in association with immediate hypersensitivity to inhaled allergens and are associated with a familial tendency toward various forms of hypersensitivity, a condition known as atopy. The etiology of allergic diseases is unknown; however there are numerous cellular and humoral defects including a raised total IgE and multiple positive specific IgE antibodies to a wide range of allergens. Although many concepts of pathogenesis are currently explored, the general treatment of allergic diseases is still unsatisfactory. Immunosuppressants like steroid and cyclosporine have been administered to patients with clinical improvement. However, their toxic effects to the hepatic and renal system. Therfore, the use of immunosuppressants in children has been reduced. Even with the effective treatment which have significant side effects there is still a proportion of patients who are recalcitrant to all forms of drugs.

Threr is evidence that exposure to indoor allergens is a causative factor for the development of asthma among individuals who are genetically predisposed to make IgE antibody (ab) response. Allergens derived from house dust mites have been recognized as an important cause of IgE ab responses for over 30 years, and Dermatophagoides species (family Pyroglyphidae) are the predominant fauna in house dust worldwide. At least some groups of protein allergens have been defined and cloned Dermatophagoides spp, and used in etiological studies investigating the role of dust mite in asthma (1–7).

The main characteristic of the allergic diathesis is the propensity to develop a sustained immunoglobulin E (IgE) response to common environmental antigens (Ag) (8). IgE production is highly dependent on IL-4 and strongly inhibited by IFN-r. Other cytokines, such as IL-5, IL-6, IL-8, IL-12 and IL-13, as well as cell-surface molecules such as CD40 and CD23, may be involved (9–11). Recent studies using bronchoalveolar lavage fluids show that the production of IgE can be regulated by suppressor T cells (12). Furthermore, a successful outcome of immunotherapy has been associated with the development of suppressor T cells which can down-regulate the allergic responses (13). There is also evidence for a defect in suppressor T-cell function in atopic subjects, particularly children with allergic asthma. Recent data from animal experiments have also revealed that functionally distinct subsets of $CD8^+$ T cells may play an important regulatory role in IgE production and suppress allergen-induced airway hyperresponsiveness (AHR) (14–17). It is therefore possible to generate Ag-specific suppressor T cells to modulate the IgE antibody response and AHR in atopic patients.

Previous methods of subunit vaccination have used purified proteins or viral vectors. Each of these methods has substantial limitations such as protein production and its purification procedures that would be overcome if the immunizing protein could be expressed in host cells. In this regard, gene vaccines represent a new approach to the development of subunit vaccines. The intramuscular injection of DNA has previously been shown to result in the expression of the protein encoded by the DNA (18–20). Furthermore, results indicate that the plasmid DNA persist episomally without replication or incorporation into the host cell genome (21). Serious inflammatory reactions at E the site of inoculation or other complications have not been observed.

In addition, it is well established that peptides derived from intracellular Ags are generally presented to $CD8^+$ T cells by major histocompatibility complex (MHC) class I molecules, which are expressed on virtually all somatic cells, while peptides derived from extracellular Ags are presented to $CD4^+$ T cells by MHC class II molecules normally expressed by specialized, Ag-presenting cells (22).

Down-regulation of immune responses to inert nonpathogenic Ag is central to the maintenance of immunologic homeostasis at mucosal surfaces in the respiratory and gastrointestinal tracts, and failure of the underlying control mechanism(s) has been suggested as a key etiologic factor in allergic diseases. An important component of this process is the selective suppression of Th2-dependent IgE response to inhaled or fed Ags, which is mediated by Ag-specific $CD8^+$ T cells (23).

Previous reports showed that $CD8^+$ T cells, which have long been regarded simply as cytotoxic cells, play a more active role in the regulation of the immune response. $CD8^+$ T cells may regulate IgE production by suppressing IgE synthesis via the inhibitory effect of IFN-r on B cells and/or by affecting the differentiation and function of Th2-like $CD4^+$ T cells, which support IgE production. An alternative explanation may be that $CD8^+$ T cells interact physically with B cells or $CD4^+$ T cells and may provide suppressive signals through cognate interaction (24).

At present, it requires a means of introducing allergen into the endogenous Ag-processing pathway to induce the production of Ag-specific $CD8^+$ T cells and inhibit allergen-specific IgE synthesis for the prevention and/or treatment of allergic disease.

SUMMARY OF THE INVENTION

The invention relates to a novel recombinant plasmid comprising an eukaryotic expression vector and an allergen gene and the pharmaceutical composition thereof.

The invention also relates to a novel recombinant plasmid comprising an eukaryotic expression vector and *Dermatophagoides pteronyssinus* mite allergens and the pharmaceutical composition thereof.

The invention also relates to a novel recombinant plasmid comprising an eukaryotic expression vector and glutathione S-transferase of *Schistosoma japonicum* worm and the pharmaceutical composition thereof.

The invention furthermore relates to the above recombinant plasmids and the pharmaceutical compositions thereof for use in inducing the production of Ag-specific $CD8^+$ T cells and/or INF-r.

The invention furthermore relates to the above recombinant plasmids and the pharmaceutical compositions thereof for use in inhibiting the production of IL-4 and/or allergen-specific IgE synthesis.

The invention furthermore relates to the above recombinant plasmids and the pharmaceutical compositions thereof for use in the prevention and/or treatment of allergic diseases.

The invention furthermore relates to the above recombinant plasmids and the pharmaceutical compositions thereof for use in the prevention and/or treatment of allergic asthma, allergic rhinitis, atopic dermatitis, food allergy and anaphylaxis.

In addition, the invention relates to a method for use in the prevention and/or treatment of allergic diseases.

The invention furthermore relates to a method for use in inducing the production of Ag-specific $CD8^+$ T cells and/or INF-r.

The invention furthermore relates to a method for use in inhibiting the production of IL-4 and/or allergen-specific IgE synthesis.

Term Definition

The term "allergen gene" used herein refers to a piece of DNA or RNA that acts as the unit controlling the formation of antigen that causes allergy in a genetically predispose person.

The term "eukaryotic expression vector" used herein refers to a piece of DNA which acts as a vehicle to taxi a foreign gene into and translate the gene into a protein in an eukaryotic cell.

Microorganism Deposit

The related microorganisms, plasmids pCMVD and pCMVG were deposited with Food Industry Research and Development Institute (FIRDI), Hsinchu, Taiwan, R.O.C. under number FIRDI 94014 and 94015 on Apr. 2, 1996 and with American Type Culture Collection (ATCC), under number ATCC 97499 and 97498 on Apr. 1, 1996.

BRIEF DESCRIPTION OF THE DRAWINGS

This application contains at least one drawing in color. Copies of this patent with color drawing(s) will be provided by the Patent and Trademark Office upon request and payment of the necessary fee.

DETAILED DESCRIPTION OF THE INVENTION

Figure 1A:
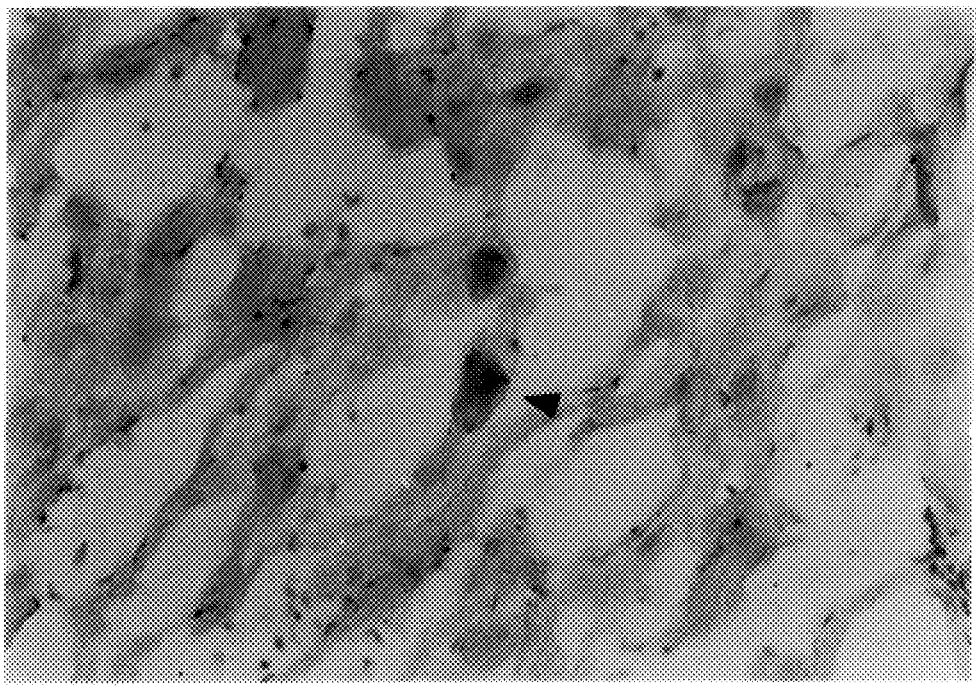
FIG. 1. In situ cytochemical staining of muscles for Der p 5 expression. Arrows indicate positively stained cells. Control muscles injected with the blank vector showed no stained muscle cells.

It has now been found that direct inoculation of a plasmid (pCMVD) encoding the *Dermatophagoides pteronyssinus* mite group 5 allergen (Der p 5) into the quadriceps muscles of mice elicits Der p 5-specific T cell and IgG responses. Such administration of plasmid DNA into mice resulted in more than 90 percent suppression of Der p 5-specific IgE synthesis, AHR in vivo following subsequent challenge of Der p 5. These effects could be transferred to naive mice by $CD8^+$ splenocytes from pCMVD-immunized mice. The main characteristic immune response of pCMVD-treated mice is the production of Der p 5-specific $CD8^+$ T cells that could inhibit the allergen-specific IgE synthesis, decreased the AHR. It is further found that direct injection of plasmid DNAs (pCMVG) encoding recombinant *Schistosoma japonicum* protein 26 (rSj26) can efficiently down-regulate in mice the rSj26-induced allergic immune response including dermatitis and rSj26-specific IgE synthesis in a dose dependent manner.

The present invention provides recombinant plasmids for use in the prevention and/or treatment of allergic diseases comprising an eukaryotic expression vector and an allergen gene.

The invention also provides recombinant plasmids for use in inducing the production of Ag-specific $CD8^+$ T cells and/or INF-r comprising an eukaryotic expression vector and an allergen gene.

The invention also provides recombinant plasmids for use in inhibiting the production of IL-4 and/or allergen-specific IgE synthesis comprising an eukaryotic expression vector and an allergen gene.

The prevention of allergic diseases refers to the immunoprophylaxis of allergen-induced IgE synthesis and inflammation of the target organ by immunomodulators (such as CD8, INF-r, CD4, IL-4 etc.). The treatment of allergic diseases refers to the treatment of allergen-sensitized individuals to down-regulate IgE synthesis and inflammation in the target organs by immunomodulators. The eukaryotic expression vector is selected from the group consisting of vectors with CMV promotor, RSV promotor and SV40 promotor, and is preferably pCMV. The allergen includes any environmental antigen which can induce allergic reaction in human such as mite allergens, glutathione S-transferase, pollen, animal dander, house dust and peanut etc.

The invention also provides a pharmaceutical composition for use in the prevention and/or treatment allergic diseases, for use in inducing the production of Ag-specific $CD8^+$ T cells and/or INF-r and for use in inhibiting the production of IL-4 and/or allergen-specific IgE synthesis comprising the recombinant plasmids of the invention and a pharmaceutically acceptable carrier.

The present invention also provides a method for the prevention and/or treatment of allergic diseases which comprises administrating the recombinant plasmids of the invention to an individual in need of such prevention and/or treatment.

The present invention also provides a method for use in inducing the production of Ag-specific $CD8^+$ T cells and/or INF-r which comprises administrating the recombinant plasmids of the invention to an individual in need of inducing the production of Ag-specific CD8$^+$ T cells and/or INF-r.

The present invention also provides a method for use in inhibiting the production of IL-4 and/or allergen-specific IgE synthesis which comprises administrating the recombinant plasmids compositions of the invention to an individual in need of inhibiting the production of IL-4 and/or allergen-specific IgE synthesis.

The allergic diseases include, for example, allergic asthma, allergic rhinitis, atopic dermatitis and anaphylaxis. The pharmaceutical compositions of the invention is preferably administered by intramuscular injection, intranasal delivery or intratracheal delivery. The pharmaceutically acceptable carrier may be conventional carriers useful for intramuscular injection, intranasal delivery or intratracheal delivery known in the art. For example, a physiologically acceptable buffer solution, normal saline, gold bead or liposome may be used.

Depending on the characteristics and progression of the disease to be prevented or treated in the individual and other factors such as age and physical conditions of the patient, the dosage of the recombinant plasmids ranges from about 0.01 to about 1.0 mg/kg body weight for a patient treated in accordance with the present invention.

The following examples further illustrate the present invention. It should be appreciated by those skilled in the art that the examples may be readily utilized as a basis for modifying or designing other techniques or processes for carrying out the same purposes of the present invention. Thus, for example, other delivery vehicles or techniques may be used for delivering the recombinant plasmids to a subject. It should also be realized by those skilled in the art that such equivalent processes do not depart from the spirit and scope of the invention as set forth in the appended claims.

EXAMPLES

Example 1

A. Materials and Methods

1. Animal

Female BALB/c, aged between 6 and 8 weeks, were used. They were obtained from the animal breeding center of the College of Medicine, National Taiwan University (originated from The Jackson Laboratory, Bar Harbor, Me.). Mice were age- and sex- matched for each experiment.

2. Molecular cloning of pCMVD recombinant plasmid

The Der p 5 cDNA was obtained by polymerase chain reaction amplification from clone WM as described in Lin, K. L. et al., J. Allergy Clin. Immunol. 94:989 (1994). The sequences of the 5' and 3' primers are 5'-AAAA AGATCTATCATGAAATTCATC-3' (Bgl II site underlined SEQ ID NO: 1) and 5'-ATTAAGCTTAAC TTCAATCTTT TTA-3' (Hind III site underlined SEQ ID NO: 2), respectively, encompassing the entire Der p 5 sequence. The PCR product was digested with Bgl II and Hind III and cloned into the eukaryotic expression vector pCMV2 originally derived from pcDNA3 (Invitrogen) and designated pCMVD. Plasmid propagation was first performed in SURE strain. Purification of the plasmid was then performed by the Wizard™ DNA purification system (Promega, Madison, Wis.) according to manufacturer's instructions. The quality and quantity of the DNA were analyzed by absorption at 260 and 280 nm and by agarose gel electrophoresis.

3. Immunohistochemical staining for Der p 5 allergen

Immnunostainings were performed according to the instructions of Histomouse-SPTM Kits (Zymed, South San Francisco, Calif.). Briefly, frozen sections of muscles (5 μm), after drying at room temperature, were fixed in pure cold acetone (10 min at 4° C.), and first treated with Peroxo-Block (Zymed) for 45 sec to quench the endogenous peroxidase activity. Sections were then blocked with 10% nonimmune serum for 1 h. After blocking, mAb to Der p 5 (a gift from Dr. R H. Lin, National Taiwan University) at 1 μg/ml was incubated with appropriate sections for 1 h. Der p 1 mAb (4Cl, a gift from M. Chapman, USA) was used as control antibody. Mice that were similarly injected with a blank vector were used as negative controls. All incubations were performed at 25° C. in a moist chamber. Incubation was followed by the addition of a biotinylated secondary antibody and the streptavidin-peroxidase conjugate. Signals were developed by the addition of 3-amino-9-ethylcarbazole. Finally, the slides were counterstained with hematoxylin solution.

4. Determination of Der p 5-specific IgG1, IgG2a and IgE

The amount of Der p 5-specific IgG1, IgG2a, and IgE were determined by ELISA. Protein high binding plates were coated with 100 μl of purified Der p 5 diluted in coating buffer (0.1 M NaHCO$_3$, pH 8.2) to a concentration of 5 μg/ml. After overnight incubation at 4° C., plates were washed three times and blocked with 3% (wt/vol) BSA-PBS buffer for 2 h at 25° C. Sera were used at 1:100 dilution for IgG measurement and 1:10 dilution for IgE measurement in duplicate. After overnight incubation at 4° C., either biotin-conjugated monoclonal rat anti-mouse IgE mAb (PharMinigen, San Diego, Calif.) or rat anti-mouse IgG mAb (PharMinigen) diluted in 0.05% gelatin buffer, was added for an additional hour. Avidin-alkaline phosphatase (Sigma Chemical Co., St Louis, Mo.)(1:1000) was then added and incubated for 1 h at 25° C., followed by 6 washes. The color reaction was developed with the addition of phosphatase substrate p-nitrophenyl phosphate, disodium (Sigma Chemical Co.). Plates were read in a microplate autoreader (Metertech, Taiwan) at 405 nm. Readings were referenced to commercial isotype standards which were mouse anti-TNP mAb, IgG1 (107.3), IgG2a (G155-178), and IgE (IgE-3) (PharMinigen).

5. Lymphocyte preparation and cell transfer protocol

Purified CD4$^-$ and CD8$^-$ splenocytes were obtained by magnetic activated cell sorting "MASC" (Miltenyi Biotec, Bergisch Gladbach, Germany). Briefly, splenocytes obtained from pCMVD-immunized and control mice 3 wk after immunization were incubated with superparamagnetic microbeads coated with monoclonal anti-CD4 or anti-CD8 antibody for 30 min at 4° C. and streptavidin-conjugated microbeads (Miltenyi Biotec) for additional 30 min. Labeled cells were separated from unlabeled cells using a "MACS" steelwool column placed into a magnetic field of 0.6 Tesla. The desired concentrations of splenocytes (106 per recipient) were resuspended in PBS in a final volume of 0.1 ml. The cell suspensions were injected into tail veins of age- and sex-matched syngeneic recipients. The recipients were then sensitized by intraperitoneal injection of 10 μg of Der p 5 with 4 mg of aluminum hydroxide (Wyeth Pharmaceuticals, Punchbowl, Australia). Venous blood was obtained weekly from the tail vein under anesthesia.

6. T cell proliferation assay

Cells after purification were resuspended in the complete tissue culture medium (RPMI 1640) supplemented with streptomycin (100 μg/ml), penicillin (100 U/ml), glutamine (5 mmol/L), and 10% heat-inactivated fetal calf serum. 10$^5$ cells per well were cultured with Der p 5 (15 μg/ml) in 96 well, flat bottom, tissue culture plate for 72 h. Cells were pulsed with 1 μCi of [3H] TdR for additional 18 h, and then harvested with a cell harvester. Thymidine incorporation was measured in a liquid scintillation counter (Beckman, Fullerton, Calif.).

7. Cytokine production by splenocytes from pCMVD-immunized mice

IL-4 and IFN-r were both measured by ELISA according to protocol supplied by the manufacturer (PharMinigen). IL-10 (R&D) and TGF-β (Promega) were measured with ELISA Kits according to the manufacturer's protocols.

8. Aerosol exposure and analysis of pulmonary resistance.

Mice were sensitized with 10 μg of Der p 5 i.p. and challenged with ultrasonic nebulization of 0.1% of Der p 5 diluted in PBS 21 days after sensitization. The inhalation challenge were perfomed in 1-L chamber connected to a DeVilbiss pulmosonic nebulizer (Model no1 2512; DeVilbiss Corp., Somerset, Pa.), which generated an aerosol mist. 8–18 hr after aerosol exposure, mice were anesthetized with Promaz i.p., and intubated with a 20-guage tracheal cannula. Changes in esophageal pressure were measured using a saline-filled catheter (PE60) and a differential pressure transducer (DP45-14, Validyne Engineering Corp., Northridge, CA). The esophageal catheter was advanced into the esophagus of the mouse until a clear cardiac artifact was discernible. Ventilation was monitored at the trachea by a pneumotachograph (Fleisch 00000, Zabona, Basel, Switzerland) connected to a differential pressure transducer (MP45-14, Validyne). The signals from the transducer were connected to a computer and analyzed with a digital electornic pulmonary monitoring system (PMS, Mumed, London, U.K.) which calculate lung resistance (RL) and dynamic compliance (Ddyn) in real time. Experimental data were stored electronically, and experimental traces or processed data were plotted on a laser printer as required. Acetylcholine (Ac) were administered intravenously with a starting dose of 1.25 mg/kg. The average volume per Ac dose was 10 μl. Twofold-increase concentrations of Ac were admininstered approximately 5 minutes apart and only after transpulmonary pressure and volume had returned to within 10% of the baseline from the previous dose, and before the next dose was administered. Intravenous saline in 10 μl was administered before the first dose of Ac to establish baselin values. Ac dose-response curves for Der p 5-sensitized or PBS Sham-sensitized groups were obtained by calculting the mean±standard error for the percent change from baseline for individual animals at each Ac dose.

9. Bronchoalveolar lavage and cell counting

After measurement of lung-function parameters, mice were lavaged with 5×0.5-ml aliquots of 0.9% sterile saline through a polythene tube introduced through the tracheostomy. Lavage fluid was centrifuged (500 g for 10 min at 4° C.), and the cell pellet was resuspended in 0.5 ml of HankÆs balanced salt solution. Total cell counts were made by adding 10 μl of the cell suspension to 90 μl of Kimura stain and counted under a light microscope in a Neubauer chamber. Differentiated cell counts were made from cytospin preparations stained by May-Grunwald stain. Cells were identified and differentiated into eosinophils, lymphocytes, nertrophils, and macrophages by standard morphologic techniques, and 500 cells were counted under magnification 400. and the percentage and absolute number of each cell type were calculated.

B. Results

1. Immune responses of plasmid pCMVD DNA immunization

Figure 1B:
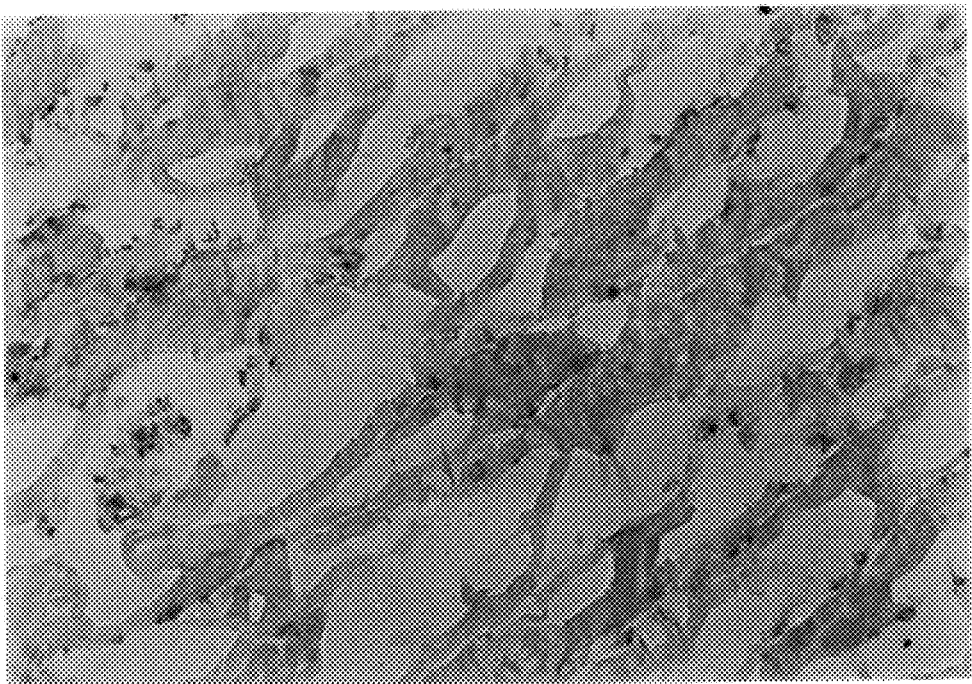
Figure 2A:
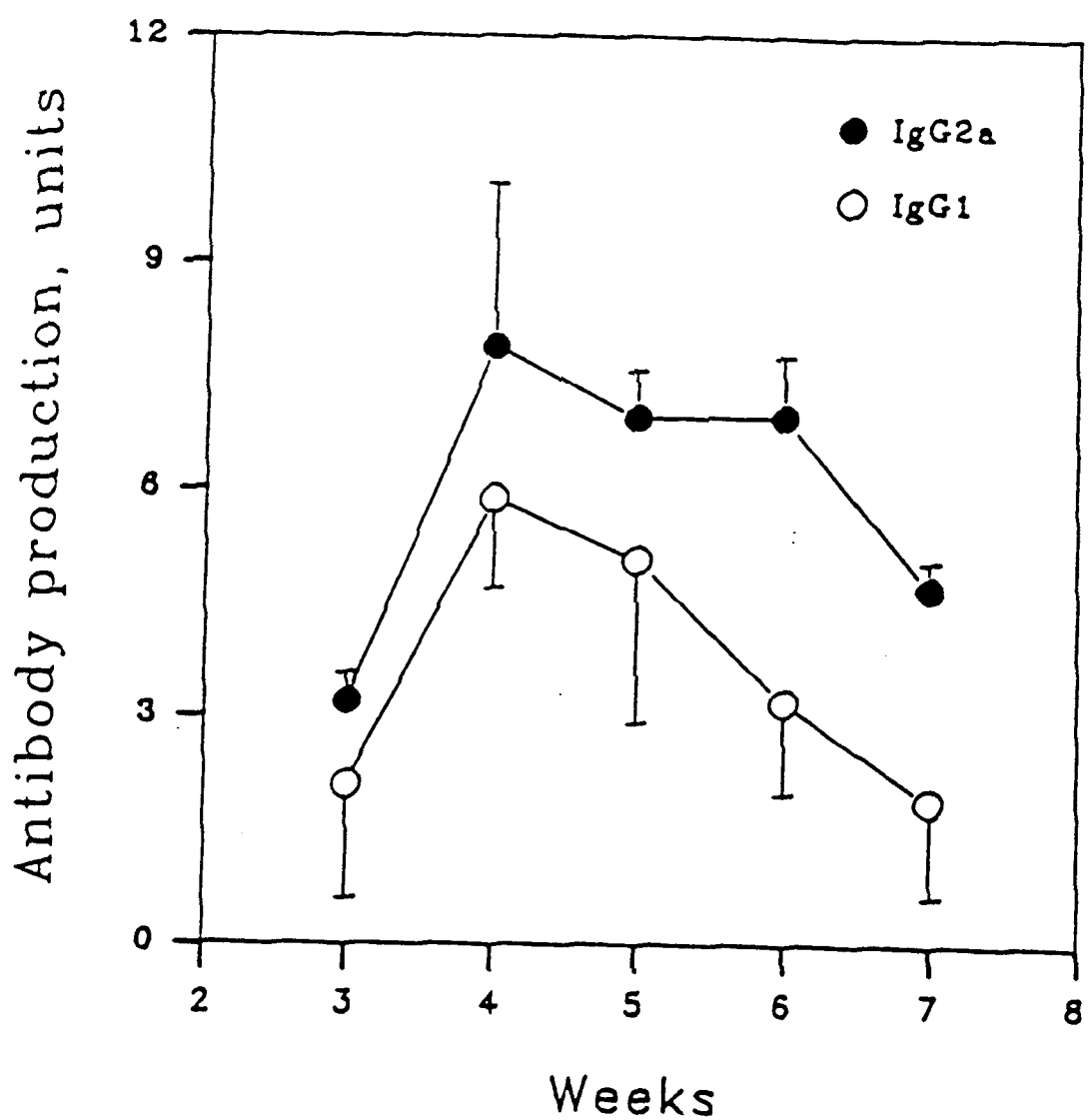
FIG. 2. (A) Immune responses after i.m. injection of pCMVD. There was no detectable Der p 5specific IgE in this group. Mice injected with the blank vector had no Der p 5-specific immune responses. One unit of antibodies corresponds to 1 ug of IgGl/ml and 1 ug of IgG2a/ml. (B) In vitro proliferation response of splenocyte subsets from pCMVD-immunized mice. Data shown are the mean ±SD of triplicate cultures.

100 μg of pCMVD in PBS was injected into the quadriceps of female BALB/c mice. Control animals were injected with PBS or the appropriate blank vector lacking the inserted Der p 5 gene. Gross cryostat sections of a muscle taken 12 days after injecting 100 ug of pCMVD DNA was stained with mAb to Der p 5 (A) or Der p 1 (B) at ×200 optical magnification. The sections were counterstained with hematoxyline. Similar results have been obtained in six individual injection sites. The expression of the transferred gene in muscle cells was confirmed by in-situ cytochemical immunostaining using anti-Der p 5 mAb 12 days after immunization (FIG. 1). In addition, Ag-specific immune responses were indicated by production of Der p 5-specific IgG1 and IgG2a antibodies, which peaked at 4 weeks after immunization, and then decreased gradually. Der p 5-specific IgE antibodies were undetectable in immunized mice (FIG. 2A).

2. Allergen-specific T cell responses in vivo

Figure 2B:
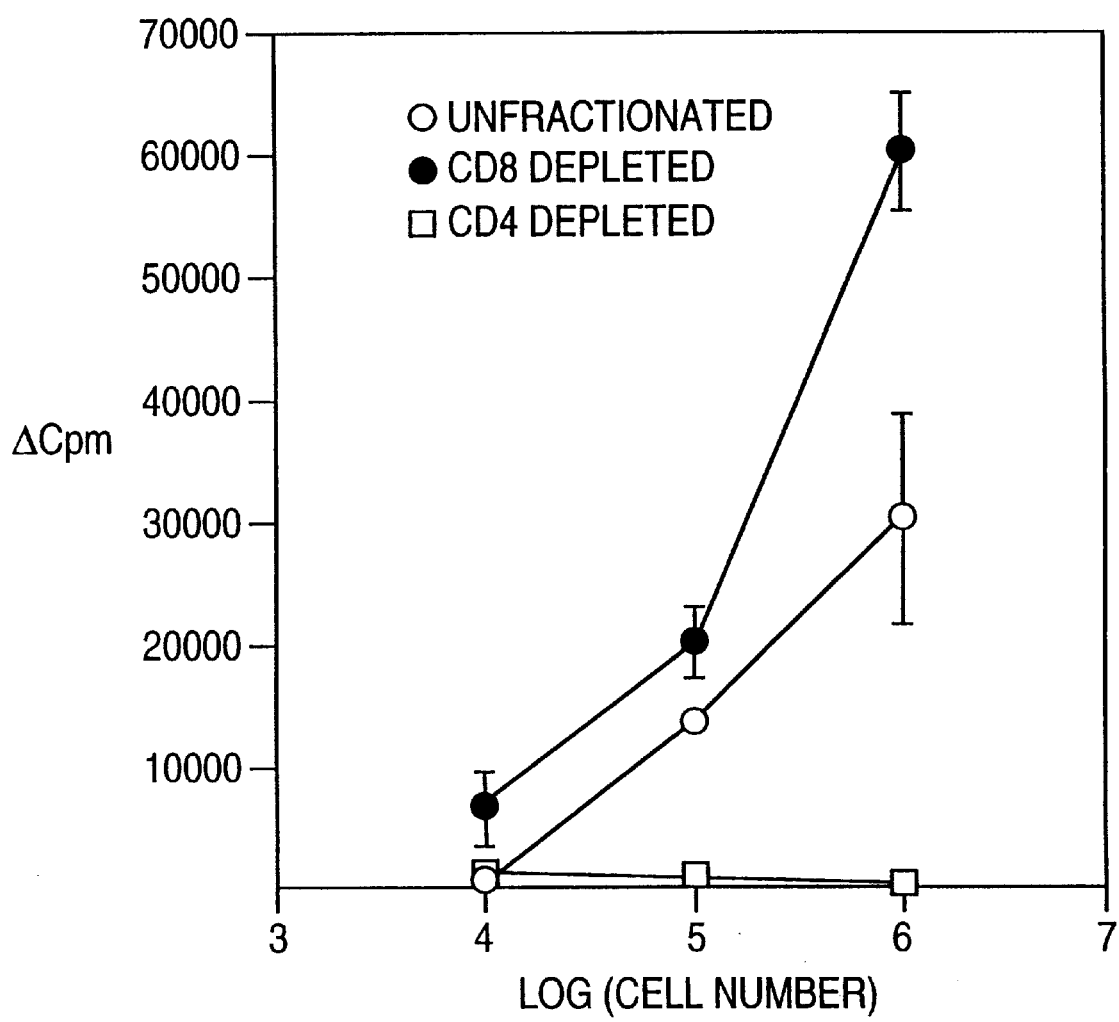

Splenocytes from immunized mice were obtained 3 weeks after immunization. The depletion of subsets was performing. According to FAScam analysis, the purified cell populations were shown to contain less than 0.5% contaminating cells. Then $CD4^+$ or $CD8^+$ cells from spleens of naive BALB/c mice were added to the cell preparations to replace the depleted cells. Cells were cultured with Der p 5 (15 μg/ml) for 72 hours. Proliferation was assayed by [$^3$H]-thymidine incorporation. Der p 5specific T cell responses were demonstrated three weeks after immunization (FIG. 2B). Furthermore, the proliferative response to Der p 5 Ag shown by unfractionated splenocytes, was suppressed by depletion of $CD4^+$ cells, but enhanced by depletion of the $CD8^+$ cells, suggesting that $CD4^+$ cell proliferation is inhibited by the $CD8^+$ population. In the same experiment, cells did not proliferate in response to Der p 1 stimulation.

3. Inhibition of allergen-specific IgE response in vivo

Figure 3A:
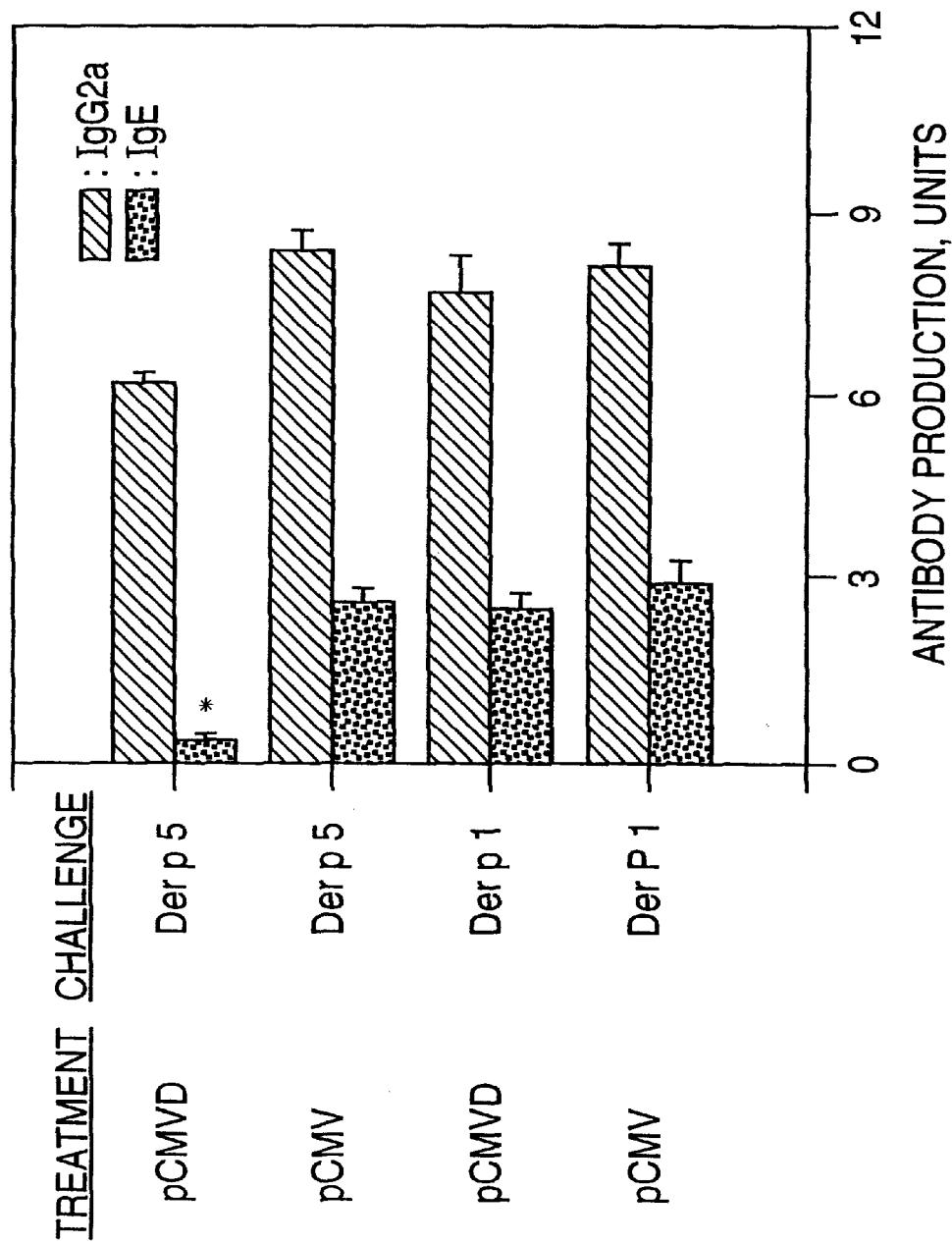
FIG. 3. (A) Inhibition of specific IgE responses by pCMVD injection (i.m.) in an Ag-specific manner. Data shown are the mean ±SD (n=6 per group) at day 21 after challenge. Asterisk * represents P<0.01. (B) Suppression of Der p 5-specific IgE responses by adoptive transfer of splenic cells from pCMVD-immunized mice. Data shown are the mean ±SD (n=6 per group) at day 21. Asterisk * represents P<0.01. One unit of antibodies corresponds to 1 ug of IgG2a/ml, and 100 ng of IgE/ml.

Both pCMV vector and pCMVD-treated mice were challenged intraperitoneally with allergen Der p 5 (10 μg with alum) or Der p 1 (10 μg with alum) three weeks after immunization. The presence of anti-Der p 5 IgE and Antigen-specific IgG2a and IgE titers in the serum were assayed by an ELISA three weeks after allergen challenge. Der p 5-specific IgE increased significantly in the vector-treated group; in contrast, pCMVD-treated mice showed more than 90% inhibition of Der p 5-specific IgE synthesis (FIG. 3A). The inhibition of IgE synthesis by pCMVD DNA injection was specific to Der p 5, because pCMVD-treated mice challenged with another mite allergen, Der p 1, could produce Der p ispecific IgE. Thus, direct gene transfer could inhibit an in vivo allergen-specific IgE synthesis efficiently and in an allergen-specific manner.

4. T cell effects on the inhibition of allergen-specific IgE response

Figure 3B:
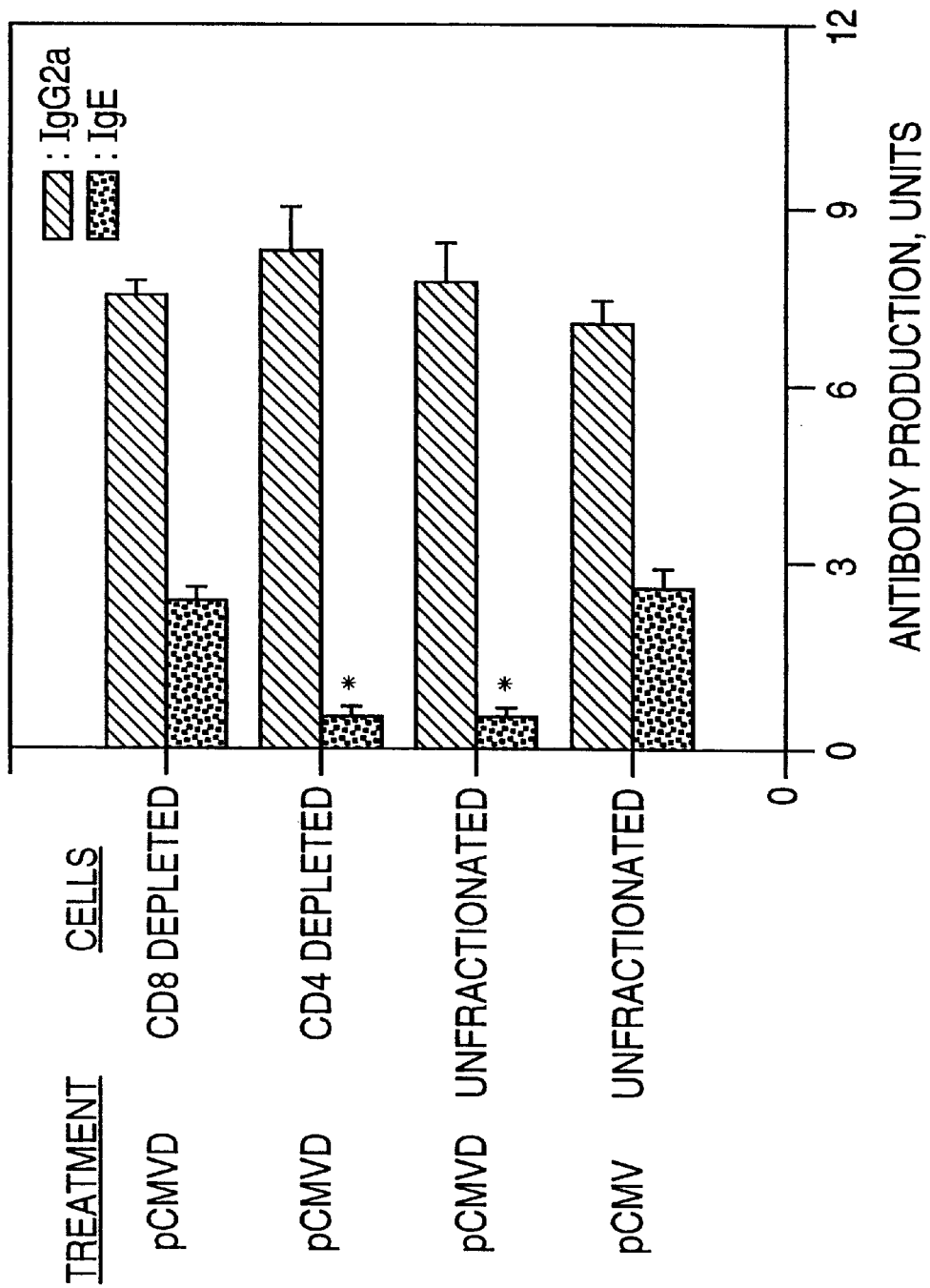

Because Ag expressed endogenously is usually presented by MHC class I molecules and triggers $CD8^+$ T cells, we therefore examined whether suppression of Der p Sspecific IgE in vivo was caused by $CD8^+$ T cells. Mice were intramuscularly injected with 100 μg of pCMV or PCMVD, and sensitized with Der p 5 or saline 3 weeks later. Three weeks after sensitization, mice received inhalation challenge with Der p 5 or saline. 18 hrs after inhalation, pulmonary resistance was determined. Unfractionated, $CD8^+$-depleted, or $CD4^+$-depleted splenocytes were adoptively transferred to naive recipients. The recipients were then challenged with Der p 5 and alum adjuvant, and Der p 5-specific IgG2a and IgE responses were determined. Both CD4⁻ cells and the unfractionated group showed significant inhibition of Der p 5-specific IgE production. In contrast, the CD8⁻ group demonstrated no inhibitory effects, indicating that CD8⁺ T cells could down-regulate the ongoing production of IgE (FIG. 3B).

5. Cytokine production involved in the inhibition of allergen-specific IgE response Because previous studies have indicated that CD8⁺ T cells could suppress Ag-specific antibody responses by killing Ag-reactive B cells or by producing soluble factors, such as IFN-r, IL-4, IL-10, and TGF-9, we investigated the in vitro activation and cytokine production by splenic T cells from pCMVD-treated mice. Spleens of mice were removed 3 weeks after immunization with pCMVD and cultured with Der p 5. Supernatants were collected after 48 h culture and analyzed by ELISA for the concentrations of IFN-r, IL-4, IL-10, and TGF-S. Unfractionated splenocytes from DNA immunized mice secreted high levels of IFN-r in response to specific Ag, and this response was markedly reduced by depletion of CD8⁺, but not CD4⁺ cells. At the same time, a small amount of IL-4 was produced by the CD8⁺ population. In contrast, IL-4 and IL-10 production was more marked in the CD4⁺ population. There was no difference in TGF-β production between these two groups, as shown in Table 1.

Table 1. Cytokines production by splenocytes from pCMVD-treated mice. Four groups of BALB/c mice, (n=3 per group), were immunized with plasmid pCMVD. Three weeks after immunization, splenocytes were cultured with recombinant Der p 5 (15 μg/ml) as indicated. Culture supernatants were collected at 48 hours for IFN-r, and IL-4 and at 72 hours for TGF-6 and IL-10 for cytokine concentrations determination by ELISA. Results represent pooled data from two independent experiments and are expressed as mean ±SD.

| Cells | Cytokine secretion | | | |
|---|---|---|---|---|
| | IFN-r (ng/ml) | IL-4 (pg/ml) | IL-10 (U/ml) | TGF-β (pg/ml) |
| Unfractionated | 16.5 ± 2.3 | 870.4 ± 130.5 | 3.96 ± 0.4 | 362.0 ± 27.5 |
| CD4⁻ | 11.4 ± 1.6 | 198.6 ± 46.3 | 1.08 ± 0.3 | 219.3 ± 21.4 |
| CD8⁻ | 0.9 ± 0.5 | 719.1 ± 58.6 | 4.02 ± 0.5 | 365.2 ± 30.2 |
| Media | 0.7 ± 0.4 | 15.1 ± 8.0 | 0.39 ± 0.2 | 365.1 ± 20.4 |

6. Immunoprophylaxis of allergen-induced AHR by allergen-gene transfer

Figure 4:
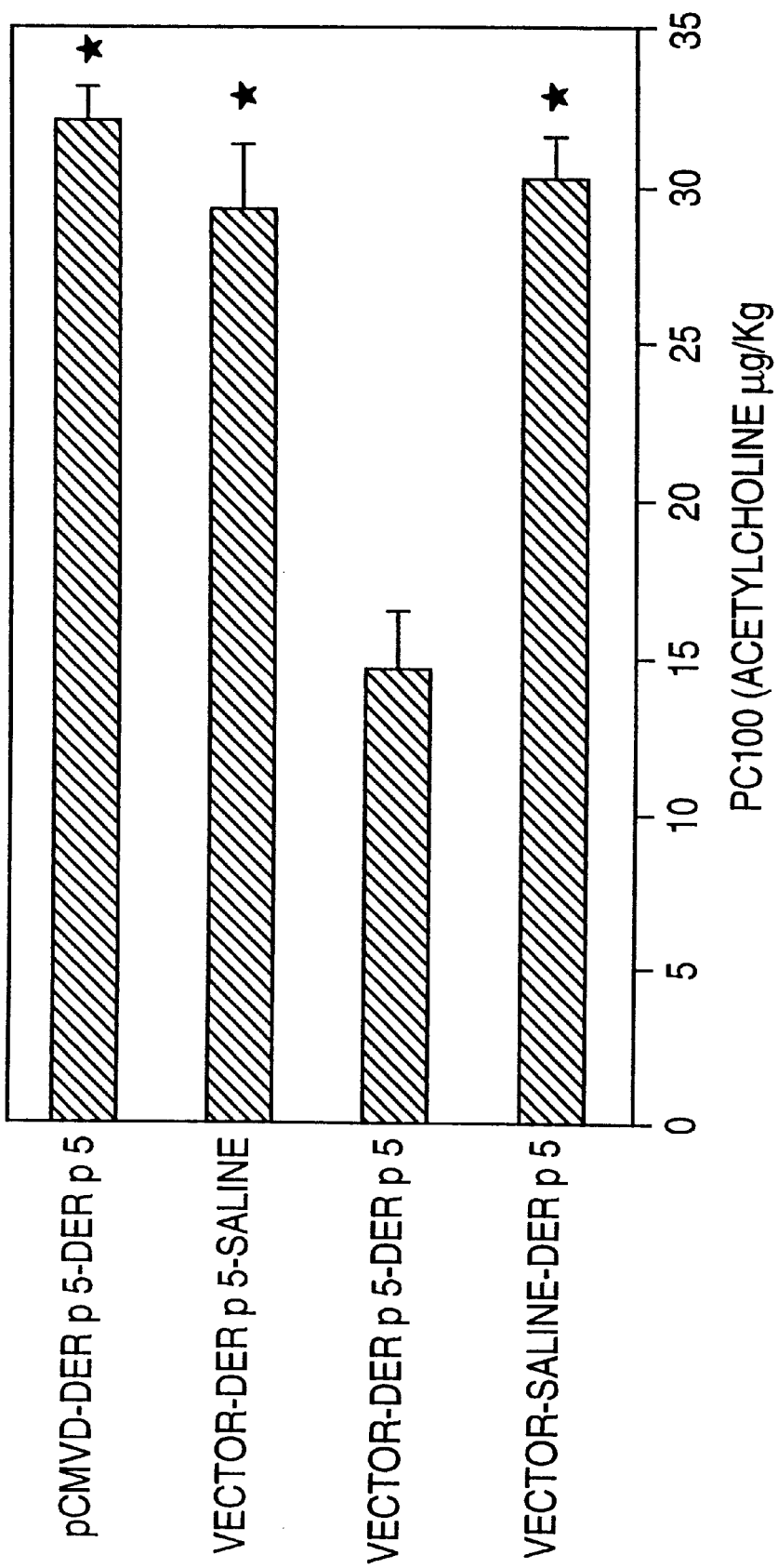
FIG. 4. Immunoprophylaxis of airway hyperreactivity by allergen-gene transfer. PC100 represents a acetylcholine amount of increasing 100% airway constriction. Asterisk * represents P<0.01.

Mice were sensitized with Der p 5 i.p. and then treated with varying dose of pCMVD plasmid DNAs 2 weeks after sensitization (3 μg, 30 μg, 100 μg). One week after treatment with plasmid, mice received inhalation challenge and pulmonary resistance were measured. We determined the pulmonary resistance (RL) after aerosol challenge with Der p 5 from ultrasonic nebulizer. In the pCMV-immunized mice, Der p 5-sensitized mice demonstrated a significant decrease acetylcholine dose (14.6±0.5) in PCIOO, compared to pCMVD-immunized mice (31.9±1.2) and sham-sensitized mice (30.2±1.3). (FIG. 4). Taken together, in addition to suppression of allergen-induced IgE synthesis, direct gene transfer also can suppress allergen-induced AHR.

7. Suppression of allergen-induced AHR by direct allergen-gene transfer

Figure 5:
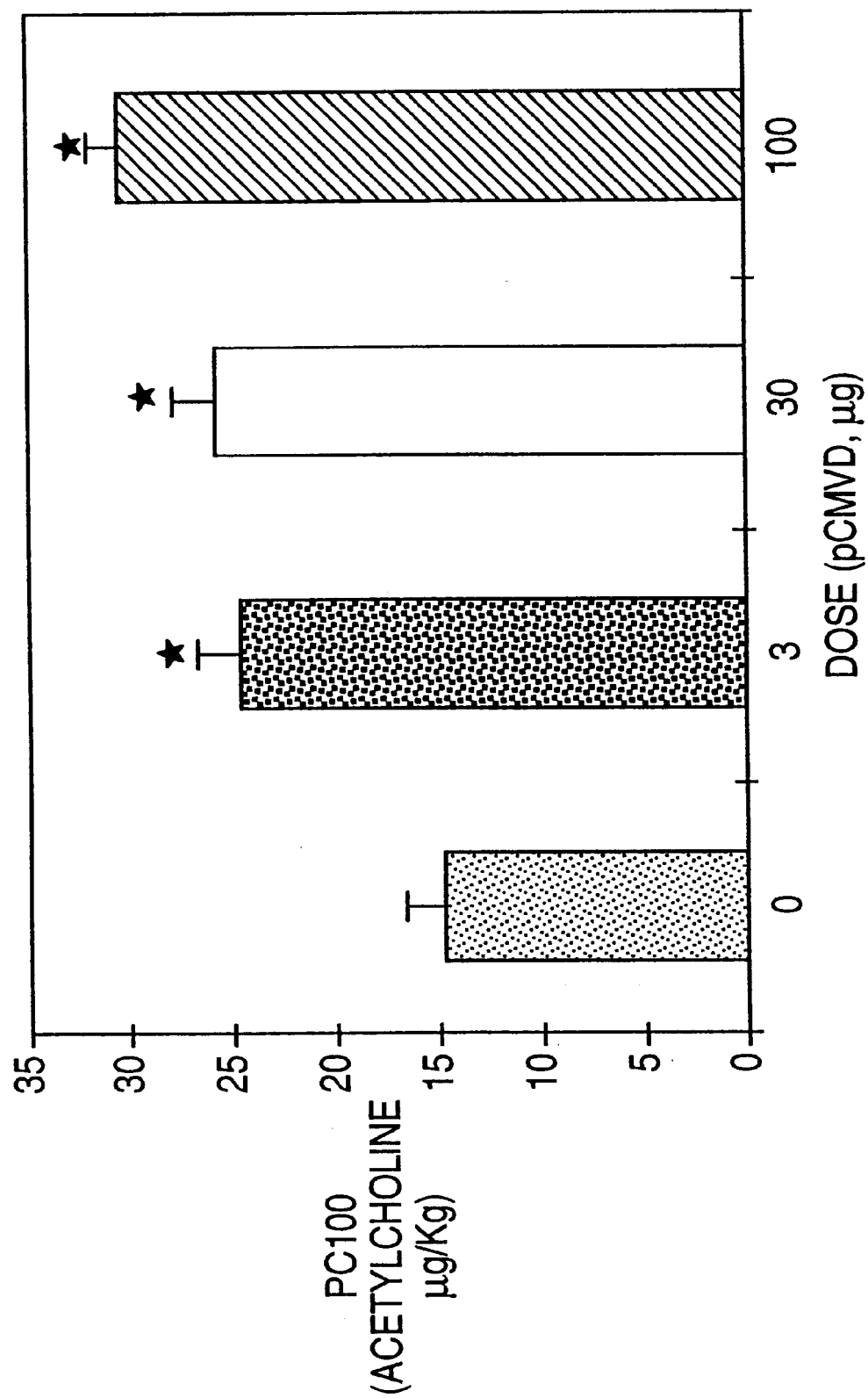
FIG. 5. Suppression of allergen-induced airway hyperreactivity by allergen-gene transfer. PC100 represents a acetylcholine amount of increasing 100l airway constriction. Asterisk * represents P<0.01.

Because most individuals are sensitzed by allergen before therapy, we further examed whether direct gene transfer could down-regulate AHR in allergen-sensitized mice. Mice were first sensitized by 10 μg of Der p 5 i.p. with alum. and then treated with varying dose of pCMVD plasmid DNAs 2 weeks after sensitization. One week after allergen-gene transfer, mice received inhaltion challenge and pulmonary function test. Allergen-gene transfer showed significant effects to AHR, compared to the sham-treated mice. Therefore direct allergen-gene transfer can down-regulate allergen-induced AHR. (FIG. 5)

Figure 6:
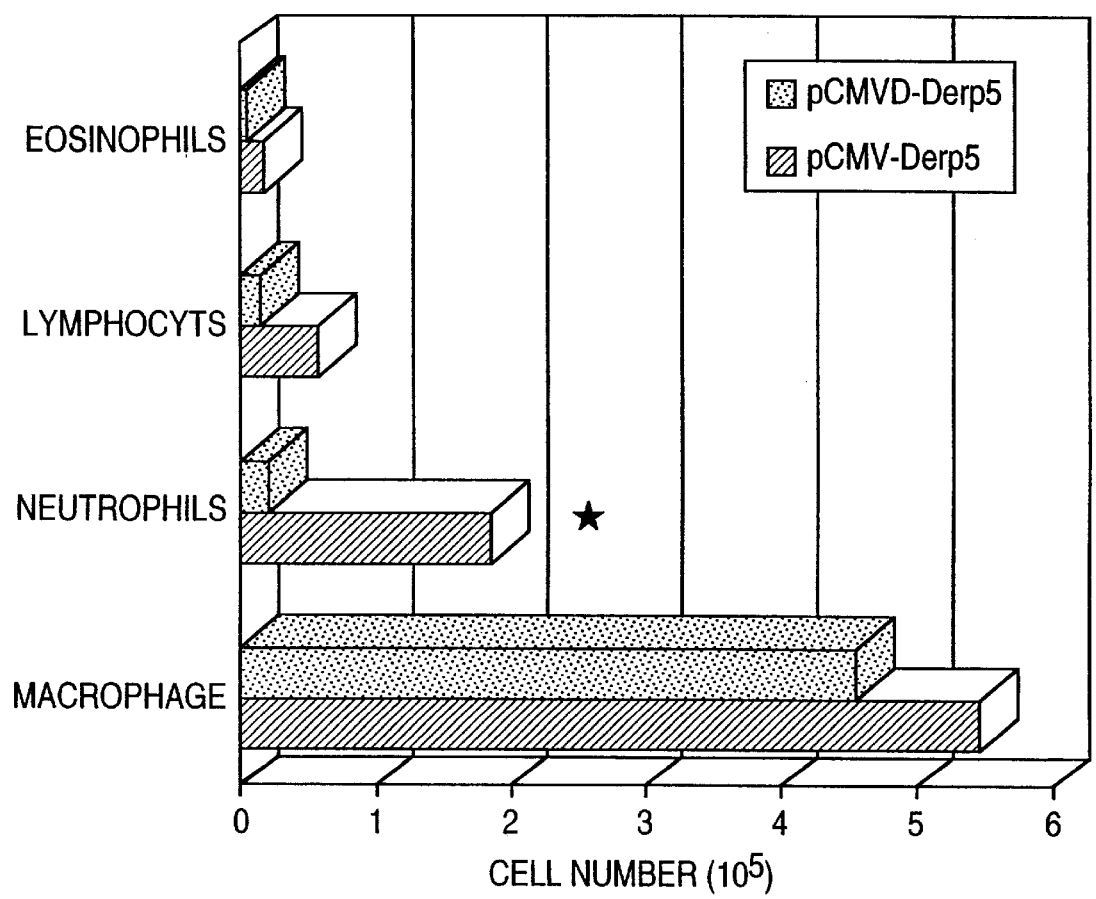
FIG. 6. Suppression of allergen-induced airway inflammation by allergen-gene transfer.
Figure 7:
FIG. 7. Gross picture of mice treated with pCMVG (right) and pCMV (left).
Figure 8:
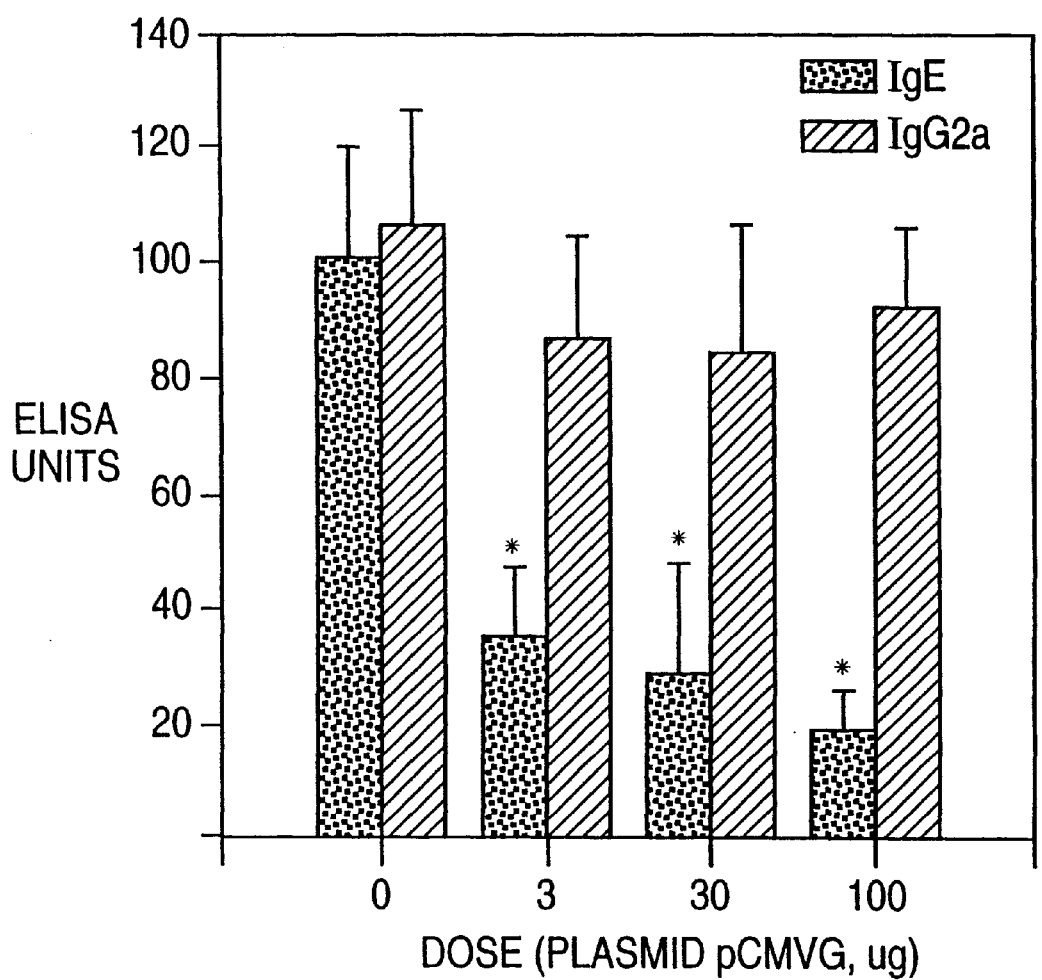
FIG. 8. Suppression of allergen-induced IgE synthesis by allergen-gene transfer. Asterisk * represents Pa 0.01.

8. Suppression of allergen-induced airway inflammation by direct allergen-gene transfer In addition to measurement of lung function, we further perfomed bronchoaveolar larvage to elucidate the pathogenesis of allergen-induced AHR and determine the effects of allergen-gene transfer to cell infiltration in the airway. Mice received bronchoaveolar larvage after measurement of lung function. Compared to sham-treated mice, neutrophils decreased significantly in pCMVD-treated mice to represent effective inhibition of airway inflammatory. compared to sham-treated mice. (FIG. 6)

Example 2

A. Materials and Methods

1. Animal

Female BALB/c, aged between 6 and 8 weeks, were obtained from the animal-breeding center of the College of Medicine, Natural Taiwan University (originated from The Jackson Laboratory, Bar Harbor, Me.). Mice were age- and sex-matched for each experiment.

2. Molecular cloning of pCMVG recombinant plasmid

The rSj26 cDNA was obtained by polymerase chain reaction amplification from pGEX2 as described previously. The sequences of the 5' and 3' primers are 5'-TAAC AGATCTATGTCCCCTATACTAGG-3' (Bgl II site underlined SEQ ID NO.: 2) and 5'-TAAT AACTTTGGAGGATGGTC-3' (Hind III site underlined SEQ ID NO.: 4), respectively, encompassing the entire rSj26 sequence. The PCR product was digested with Bgl II and Hind III and cloned into the eukaryotic expression vector pCMV2 originally derived from pcDNA3 (Invitrogen) and designated pCMVD. Plasmid propagation was first performed in SURE strain. Purification of the plasmid was then performed by the Wizard™ DNA purification system (Promega, Madison, Wis.) according to manufacturer's instructions. The quality and quantity of the DNA were analyzed by absorption at 260 and 280 nm and by agarose gel electrophoresis.

3. Study protocol

Mice were initially i.p. sensitized with 10 μg of rSj26 with 4 mg of aluminium hydroxide (Wyeth Pharmaceuticals, Punchbowl, Australia). Fourteen days after sensitization, mice were anesthetized by injecting 0.1 mg of PromAce (Ayerst Laboratories, New York, N.Y.) intraperitoneally. A 1.0 cm incision in the skin was made so that the underlying muscle could be directly visualized. The tip of the needle was inserted 0.2 cm deep into the quadriceps muscles. One hundred μg, 30 μg, or 3 μg of pCMVG or pCMV in 0.1 ml of PBS was injected by a 27-gauge needle connected to a 1-ml syringe, respectively. Seven days after gene transfer, mice received 1.0 μg of rSj26 challenge again. Seven days after challenge, mice were sacrificed for skin biopsy and blood sampling.

4. Purification of recombinant Sj26

Recombinant Sj26 was purified from E. coli containing a plasmid (pSj26) that directs synthesis of rSj26. E. coli were grown overnight in Luria broth containing 100 μg of ampicillin at 37° C. for 3 h with vigorous shaking. IPTC was then added to 0.1 mM and incubated for a further 3 h. The cell pellet was washed by centrifugation at 10000 g for 30 min at room temperature and resuspended in 10 mM Tris-HCl, 150 mM NaCl (TBS, pH 7.5) containing 5 mM EDTA. The cells were disrupted with 0.1 mm glass beads using a Braun homogenizer (B. Braun, Germany) in the presence of 3 TIU of aprotinin (Sigma), 0.5 mM of PMSF (Sigma) and 20 μg/ml of DNase (Boehringer). Triton X-100 (li) was added to bacterial lysate and precleared by centrifugation (40000 rpm for 20 min) and the lysate supernatant was passed through glutathione agarose column (Sigma). The rSj26 protein was eluted with 5 mM reduced glutathione in 50 mM Tris-HCl (pH 8.0) after extensive washing with TBS buffer.

5. Determination of rSj26 specific serum IgE and IgG titer

The amounts of rSj26-specific IgE, IgG1 and IgG2a were determined by ELISA. Costar high binding plates were coated with 100 μl of purified rSj26 or Der p 5 diluted in coating buffer (0.1 M $NaHCO_3$, pH 8.2) to a concentration of 5 Ag/ml. After overnight incubation at 4° C., plates were washed three times and blocked with 3% (wt/vol) BSA-PBS buffer for 2 h. at room temperature. Serum samples were diluted in gelatin buffer with a 1:100 dilution for IgG measurement and 1:10 dilution for IgE measurement and added in duplicate to the plates. For measurements of serum specific IgE, commercial standards (PharMinigen) were used, and readings were referenced to these standards. Serum samples and standards were incubated overnight at 4° C. Either biotin-conjugated monoclonal rat anti-mouse IgE MoAb (PharMinigen) or rat anti-mouse IgG MoAb (PharMinigen) diluted in 0.05% gelatin buffer was added for an additional hour. Avidin-alkaline phosphatase (Sigma) (1:1000) was then added and incubated for 1 h at room temperature, followed by 6 washes. The color reaction was developed with the addition of phosphatase substrate p-Nitrophenylphosphate, Disodium (Sigma). Plates were read in a microplate autoreader (Metertech) at 405 nm. Readings were referenced to a standard sera pooled from 4 mice which were initially injected peritoneally with 10 μg of rSj26 or Der p 5 with aluminum hydroxide and boosted 21 d with the same dose. The standard serum was calculated as 100 ELISA units/ml.

6. Histological evaluation

Each biopsy specimen was fixed with 4% formaldehyde and paraffin embedded. 5 μm sections were cut for staining with haematoxylin-eosin staining.

B. Results

1. Decrease inflammatory responses in the skin

We inject pCMVG plasmid DNAs into rSj26-sensitized mice. Skin biopsy was performed in all mice 7 days after boost injection. Histological evaluation revealed prominent inflammatory cell infiltration in the pCMV (blank vector) treated mice, but no apparent cell infiltration in the pCMVG-treated mice. In pCMVG-treated mice also showed grossly smooth skin, compared to the erythmatous and sparsely skin in the pCMV-treated mice (FIG. 7). We therefore suggest direct inject pCMVG can down-regulate the inflammation in the skin.

2. Decrease of rSj26-specific IgE by allegen-gene transfer

Mice were sensitized with 10 μg of rSj26 i.p. with alum and then treated with varying dose of pCMVD plasmid DNAs 2 weeks after sensitization (3 μg, 30μg, 100 μg). Data shown are the mean ±SD (n=6 per group) at day 7 after treatment and anti-rSj26 IgG2a and IgE titer were determined. Sj26-specific IgE decreased significantly in pCMVG-treated mice. In contrast, rSj26-specific IgG2a showed no significant difference. In addition, the inhibition of IgE synthesis by pCMVG DNA injection was specific to rSj26 allergen, because pCMVG-treated rats challenged with Der p 5, could produce Der p 5-specific IgE. Thus, direct injection of rSj26-gene can down-regulate ongoing rSj26-specific IgE synthesis in vivo (FIG. 8).

REFERENCE

1. Sporik, R., S. T. Holgate, T. A. E. Platts-Mills, and J. Cogswell. 1990. Exposure to house dust mite allergen (Der p 1) and the development of asthma in childhood: a prospective study. *N. Engl. J. Med* 323:502–507.
2. Platts-Mills, T. A. E., W. R. Thomas, R. C. Aalberse, D. Vervloet, and M. D. Chapman. 1992. Dust mite allergens and asthma: report of a second international workshop. *J. Allergy Clin. Immunol.* 89:1046–1060.
3. Peat, J. K., E. Tovey, B. G. Toelle, M. M. Haby, E. J. Gray, A. Mahmic, and A. J. Woolcock 1996. House dust mite allergens. A major risk factor for childhood in Australia. *Am. J. Respir. Crit Care Med.* 153:141–146.
4. Burrows, B., F. D. Martinez, M. Halonen, R.A. Barbee, M. G. Cline. 1989. Association of asthma with serum IgE levels and skin-test reactivity to allergens. *N. Engl. J. Med.* 320:271–277.
5. Sears, M. R., B. Burrows, E. M. Flannery, G. P. Herbison, C. J. Hewitt, and M. D. Holdaway. 1991. Relation between airway responsiveness and serum IgE in children with asthma and in apparently normal children. N. Engl. J. Med. 325:1067–1071.
6. Gelber, L. E., L. H. Seltzer, J. K. Bouzolds, S. M. Pollart, M. D. Chapman, and T. A. E. Platts-Mills. 1993. Sensitization and exposure to indoor allergens as risk factors for asthma among patients presenting to hospital. *Am. Rev. Respir. Dis.* 147:573–578.
7. Sporik, S., J. M. Ingram, W. Price, J. H. Sussman, R. W. Honsinger and T. A. E. Platts-Mills. 1995. Association of asthma with serum IgE and skin test reactivity to allergens among children living at high altitude. Ticking the dragon's breath. *Am. J. Resp. Crit. Care Med.* 151:1388–1392.
8. Roundtress, S., J. J. Cogswell, T. A. E. Platts-Mills, and E. B. Mitchell. 1985. Arch. Dis. Child. 60:727.
9. Romagnani, S. 1990. Immunol. Today 11:316.
10. Jabara H. H., S. M. Fu, R. S. Geha, and D. Vercelli. 1990. J. Exp. Med. 172:1861.
11. Sutton B. J., and H. J. Gould. 1993. Nature 366:421.
12. Hsieh K. H. 1984. 3. J. Allergy Clin. Immunol. 74:34.
13. Gonzalez, M. C., P. Diaz, F. R. Galleguuillos, P. Ancic, O. Cromwell and A. B. Kay. 1987. Am. Rev. Respir. Dis. 136:600.
14. Sedowick, J. D., & Holt, P. G. Induction of IgE secreting cells and IgE isotype-specific supppressor cells in the respiratory lymph nodes of rats in response to antigen inhalation. Cell. Immunol. 94, 182–194 (1985).
15. Kemeny, D. M., & Diaz-Sanchez, S. Role of CD8 T cells in rat IgE responses. Int. Arch. Allergy Appl. Immunol. 94, 99–101 (1991).
16. McMenamin, C., & Holt, P. G. The natural immune response to inhaled soluble protein antigens involves major histocompatibility complex (MHC) Class I-resticted $CD8^-$ T cell-mediated but MHC Class II-restricted $CD4^-$ T cell-dependent immune deviation resulting in selective suppression of immunolglobulin production. J. Exp. Med. 178, 889–899 (1993).
17. Renz, H., G. et al. Inhibition of IgE production and normalization of airways responsiveness by sensitized $CD8^+$ T -ells in a mouse model of allergen-induced sensitization. J. Immunol. 152, 351–360 (1994).
18. Wolff, J. A. et al. Direct Gene Transfer into Mouse Muscle in Vivo. Science. 247, 1465–1468 (1990).
19. Tang, D. L. DeVit M., & Johnston S. A Genetic immunization is a simple method for eliciting an immune response. Nature 356, 152–154 (1992).
20. Ulmer, J. B. et al. Heterologous protection against influenza by injection of DNA encoding a viral protein. Science. 259, 1745–1749 (1994).

21. Wolff J. A. et al. Long-term persistence of plasmid DNA and foreign gene expression in mouse muscle. 6, 363–369 (1994).
22. Brodsky, F. M., & Guagliardi, E. The cell biology of antigen processing and presentation Ann. Rev. Immuno. 9, 707–744 (1991).
23. Holt, P. G., & Sedgwick, J. D. Suppression of IgE responses following antigen inhalation: a natural homeostatic mechanism which limits sensitization to aeroallergens. Immunol. Today 8, 14–18 (1987).
24. Kemeny, D. M., A. Nobler, B. J. Holmes and D. Diaz-Sanchez 1994. Immunol. Today 15:107.

What is claimed is:

1. A vaccine for prophylactic treatment of allergic asthma comprising a pCMVD vector which comprises a gene encoding dust mite allergen, and a pharmaceutically acceptable carrier.

2. A pharmaceutical composition for the treatment of allergic asthma comprising a pCMVD vector which comprises a gene encoding dust mite allergen, a pharmaceutically acceptable carrier.

3. A vaccine for prophylactic treatment of allergic asthma comprising the non-viral, eukaryotic expression vector pCMVD which comprises a gene encoding dust mite allergen, and a pharmaceutical acceptable carrier, wherein the pharmaceutical carrier is selected from the group consisting of normal saline and liposomes.

4. A pharmaceutical composition for the treatment of allergic asthma comprising the non-viral, eukaryotic expression vector pCMVD which comprises a gene encoding dust mite allergen, and a pharmaceutical acceptable carrier, wherein the pharmaceutical carrier is selected from the group consisting of normal saline and liposomes.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR Primer"

(ix) FEATURE:
       (A) NAME/KEY: misc_feature
       (B) LOCATION: 5..10
       (D) OTHER INFORMATION: /label= BglII-site (ix) FEATURE:
       (A) NAME/KEY: misc_feature
       (B) LOCATION: 1..25
       (D) OTHER INFORMATION: /note= "PCR primer for Der p 5 cDNA
          cloning"

(xi) SEQUENCE DESCRIPTION: SEQ ID NO:1:

AAAAAGATCT ATCATGAAAT TCATC                                    25

(2) INFORMATION FOR SEQ ID NO:2:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR Primer"

(ix) FEATURE:
       (A) NAME/KEY: misc_feature
       (B) LOCATION: 4..9
       (D) OTHER INFORMATION: /label= HindIII-site (ix) FEATURE:
       (A) NAME/KEY: misc_feature
       (B) LOCATION: 1..25
       (D) OTHER INFORMATION: /note= "PCR Primer for Der p 5 cDNA"

(xi) SEQUENCE DESCRIPTION: SEQ ID NO:2:

ATTAAGCTTA ACTTCAATCT TTTTA                                    25

(2) INFORMATION FOR SEQ ID NO:3:

(i) SEQUENCE CHARACTERISTICS:
       (A) LENGTH: 27 base pairs
       (B) TYPE: nucleic acid
       (C) STRANDEDNESS: single
       (D) TOPOLOGY: linear (ii) MOLECULE TYPE: other nucleic acid -continued

```
            (A) DESCRIPTION: /desc = "PCR Primer"

(ix) FEATURE:
            (A) NAME/KEY: misc_feature
            (B) LOCATION: 5..10
            (D) OTHER INFORMATION: /label= BglII-site (ix) FEATURE:
            (A) NAME/KEY: misc_feature
            (B) LOCATION: 1..27
            (D) OTHER INFORMATION: /note= "PCR Primer for rSj26 cDNA"

(xi) SEQUENCE DESCRIPTION: SEQ ID NO:3:

TAACAGATCT ATGTCCCCTA TACTAGG                                              27

(2) INFORMATION FOR SEQ ID NO:4:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "PCR Primer"

(ix) FEATURE:
            (A) NAME/KEY: misc_feature
            (B) LOCATION: 5..10
            (D) OTHER INFORMATION: /label= HindIII-site (ix) FEATURE:
            (A) NAME/KEY: misc_feature
            (B) LOCATION: 1..22
            (D) OTHER INFORMATION: /note= "PCR Primer for rSj26 cDNA"

(xi) SEQUENCE DESCRIPTION: SEQ ID NO:4:

TAATAAGCTT TGGAGGATGG TC                                                   22
```